United States Patent
Li et al.

(10) Patent No.: US 11,365,408 B2
(45) Date of Patent: Jun. 21, 2022

(54) LIBRARY PREPARATION

(71) Applicant: NUGEN TECHNOLOGIES, INC., San Carlos, CA (US)

(72) Inventors: Bin Li, Palo Alto, CA (US); Benjamin G. Schroeder, San Mateo, CA (US); Manqing Hong, Belmont, CA (US); Maureen Peterson, Oakland, CA (US)

(73) Assignee: NUGEN TECHNOLOGIES, INC., Redwood City, CA (US)

( * ) Notice: Subject to any disclaimer, the term of this patent is extended or adjusted under 35 U.S.C. 154(b) by 49 days.

(21) Appl. No.: 16/268,971

(22) Filed: Feb. 6, 2019

(65) Prior Publication Data

US 2019/0241887 A1    Aug. 8, 2019

Related U.S. Application Data

(60) Provisional application No. 62/627,577, filed on Feb. 7, 2018.

(51) Int. Cl.
*C12N 15/10* (2006.01)
*C40B 50/06* (2006.01)
*C40B 40/06* (2006.01)

(52) U.S. Cl.
CPC ..... *C12N 15/1065* (2013.01); *C12N 15/1093* (2013.01); *C40B 50/06* (2013.01); *C40B 40/06* (2013.01)

(58) Field of Classification Search
CPC ............ C12N 15/1065; C12N 15/1093; C40B 50/06; C40B 40/06
See application file for complete search history.

(56) References Cited

U.S. PATENT DOCUMENTS

| | | | |
|---|---|---|---|
| 9,650,628 | B2 | 5/2017 | Amorese et al. |
| 2006/0068415 | A1 | 3/2006 | Jones et al. |
| 2013/0157869 | A1* | 6/2013 | McReynolds ........ C12Q 1/6832 506/2 |
| 2015/0004600 | A1 | 1/2015 | Wang et al. |
| 2015/0299767 | A1 | 10/2015 | Armour et al. |

OTHER PUBLICATIONS

Nai et al. ("T Oligo-Primed Polymerase Chain Reaction (TOP-PCR): A Robust Method for the Amplification of Minute DNA Fragments in Body Fluids." Sci Rep 7, 40767 (Jan. 17, 2017), 12 pages.).*
Nugen ("User Guide: Ovation® Ultralow System V2 1-16—M01379 v3", (2015), 27 pages).*
Faircloth, 2012, Not all sequence tags are created equal: Designing and validating sequence identification tags robust to indels, PLoSONE 7(8):e42543.
Head, 2015, Library construction for next-generation sequencing: Overviews and challenges, Biotechniques 56(2):61.
International Search Report and Written Opinion dated Apr. 11, 2019, for PCT/US19/16816, filed Feb. 6, 2019 (6 pages).

* cited by examiner

*Primary Examiner* — Robert H Havlin
(74) *Attorney, Agent, or Firm* — Brown Rudnick LLP; Thomas C. Meyers

(57) ABSTRACT

The disclosure provides DNA library preparation methods that do not require a purification between adapter ligation and PCR amplification. Adaptors are added to DNA fragments to form oligonucleotide extension products and the oligonucleotide extension products are amplified without stopping or interruption for a cleanup step. Excess materials, such as enzymes, adaptors, or co-factors, from the adaptor addition step do not interfere with the amplification step and the amplification step proceeds without regards to the presence of reagents from the ligation step. In preferred embodiments, the ligation and amplification step make use of a common priming sequence e.g., in the form of one of the adaptor oligos.

18 Claims, 11 Drawing Sheets

| END REPAIR | | VOLUME |
|---|---|---|
| Program 1<br>End Repair | 25 °C – 30 min, 70 °C – 10 min, hold at 4 °C | 15 µL |
| LIGATION | | VOLUME |
| Program 2<br>Ligation | 25 °C – 30 min, 70 °C – 10 min, hold at 4 °C | 30 µL |
| AMPLIFICATION | | VOLUME |
| Program 3<br>Amplification | 72 °C – 2 min, 95 °C – 3 min, 8–15* cycles (98 °C – 20 sec, 65 °C – 30 sec, 72 °C – 30 sec), 72 °C – 1 min, hold at 4 °C | 50 µL |

FIG. 5

Using adaptors as primers avoids peak at ~ 150 bp from un-ligated adapters (Bioanalyzer trace after PCR shows no adaptor artifacts)

LIBRARY PREPARATION

TECHNICAL FIELD

The invention relates to the preparation of DNA libraries for next-generation sequencing.

BACKGROUND

Next-generation sequencing (NGS) of DNA can rapidly provide large amounts of medically important genetic information. NGS sequencing instruments operate on libraries of DNA that are prepared from clinical or biological samples. DNA library preparation often uses a commercial kit that comes with the reagents and instructions for the isolation of genes of interest. One commonly used library prep kit is the library prep kit sold under the trademark TRUSEQ by Illumina (San Diego, Calif.).

Typical library preparation kits and protocols provide for the fragmenting of input DNA followed by end repair, bead cleanup, A-tailing, adaptor ligation, bead cleanup, PCR amplification, and a final bead cleanup. The cleanup steps may proceed by other known methods, but cleanup using magnetic beads is popular as it is reasonably straightforward using commercially available kits and instructions from companies such as Agencourt.

While time consuming, bead cleanup is understood to be a necessary step in library preparation because excess reagents from one step, if not removed, will interfere with or prevent successful completion of subsequent steps. Specifically, purification is understood to be required after ligation to remove adaptors and other ligation reaction components such as high concentrations of magnesium and PEG, which are incompatible with the subsequent PCR amplification. Furthermore, existing protocols require distinct PCR primers in order to amplify a functional final sequencing library.

SUMMARY

The disclosure provides DNA library preparation methods that do not require a purification between adapter ligation and PCR amplification and in which adapter oligos can function as primers during amplification. In preferred embodiments, adaptors are added to DNA fragments and then the fragments are amplified without an intervening cleanup step. In fact, at least one oligo strand of the starting adaptors may, in some embodiments, function as an amplification primer.

In some embodiments, partially double-stranded adaptors are ligated at both ends of a DNA fragment, to the free 5' ends, after which the 3' end is extended to copy the full adapter sequence. The adaptor may be at least partially double-stranded to facilitate recognition and enzymatic by a ligase. After the fragments are extended across the major strands of the adaptors, displacing the minor strands of the adaptors, the resultant adaptor-ligated fragments are amplified by polymerase chain reaction (PCR). The disclosure includes results showing that no purification or cleanup step is required between adaptor ligation and amplification. Thus materials present for adaptor ligation may still be present during amplification including materials such as the adaptors, enzymes, co-factors, etc. Other embodiments of adaptors and adaptor addition are within the scope of the disclosure.

In certain embodiments, a first adaptor is ligated to a DNA fragment and a second adaptor hybridizes thereto, after which the second adaptor is extended through the first to form an oligonucleotide extension product which is amplified. The amplification can even use the second adaptor as a primer. The oligonucleotide extension products are amplified without stopping or interruption for a cleanup step. Excess materials, such as enzymes, adaptors, or co-factors, from the adaptor ligation step do not interfere with the amplification step and the amplification step proceeds without regards to the presence of reagents from the ligation step. In fact, in preferred embodiments, the ligation and amplification step make use of a common primer, the second adaptor oligo.

Methods of the disclosure are useful with single-primer enrichment in which target-specific primers and adaptors are used in the adaptor ligation steps and then are also used as primers in the amplification step. In such embodiments, target DNA is fragmented, and indexed forward adapters are ligated. Oligos comprising target probes and reverse adaptors are annealed to the fragments and extended. The resulting ds product is denatured and PCR primers are annealed for amplification and library enrichment.

Embodiments of the methods need no more than a single purification or bead cleanup after the PCR step. Methods of the disclosure are compatible with both mechanical and enzymatic shearing of DNA. Adaptors used according to the disclosure allow for both ligation and PCR amplification, without addition of distinct PCR primers (which are required with Illumina Y-adaptors). Thus, the disclosure provides library preparation methods in which a post-ligation bead cleanup is eliminated. Library preparation according to methods of the disclosure may proceed with no more than a single purification or bead cleanup step and generate high quality libraries for sequencing. The library preparation methods use sequencing adaptors that also serve as PCR primers. Additionally, methods of the disclosure are compatible with both enzymatic and mechanical DNA fragmentation.

Aspects of the invention provide a method of preparing a sequencing library. The method includes obtaining a plurality of DNA fragments from nucleic acid from a sample, incubating the DNA fragments with adaptor oligos to form adaptor-ligated fragments in which at least a first adaptor oligo is ligated to a fragment and at least a second adaptor oligo hybridizes to the fragment and is extended by a polymerase to form a sequence complementary to a target and complementary to the first adaptor oligo, and amplifying the DNA fragments in the presence of the adaptor oligos to form a plurality of amplicons. Copies of the second adaptor oligo function as primers during the amplification step.

In certain embodiments, the adaptor ligation and amplification includes (a) appending a first adaptor to a 5' end of each DNA fragment; (b) annealing one or more second adaptor oligos to the DNA fragments, whereby each of the one or more oligonucleotides comprise a 3' portion that is complementary to a sequence of interest present in one or more of the fragments, and a 5' portion comprising a second adapter sequence; (c) extending the one or more second adaptor oligos with a polymerase thereby generating one or more oligonucleotide extension products with the first adaptor at a first end and the second adaptor sequence at a second end; and (d) amplifying—with no intervening cleanup or purification step—the one or more oligonucleotide extension product using the second adaptor oligos as an amplification primer, to enrich for nucleic acid fragments containing the first adaptor and the second adaptor sequence at each end.

Methods optionally include purifying the amplicons to remove excess material. The amplicons may be attached to a flow cell surface to form sequencing clusters. Methods may include sequencing the amplicons to determine a sequence of the nucleic acid. In some embodiments, the methods begin with any of reverse transcribing RNA to obtain DNA nucleic acid and/or fragmenting the nucleic acid from the sample to obtain the plurality of DNA fragments.

BRIEF DESCRIPTION OF THE DRAWINGS

FIG. 5 diagrams an exemplary program for thermal cycler.

DETAILED DESCRIPTION

Figure 1:
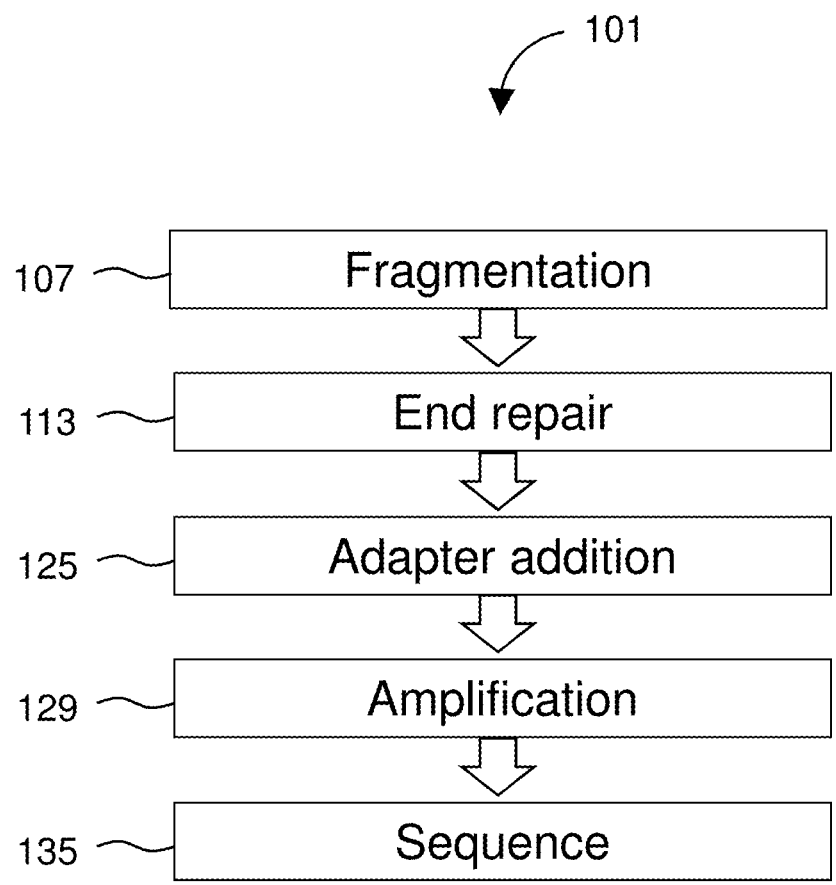
FIG. 1 diagrams a method of library preparation.

The disclosure relates to simplified library preparation methods for next-generation sequencing of nucleic acids.

Methods of the disclosure include adding adaptors to DNA fragments (e.g., by ligating a free end of an adaptor that includes at least partially dsDNA to a free 5' end of a DNA fragment, or insert) and amplifying the adaptors without an intervening cleanup step (and optionally by using an un-ligated strand from one or more of the adaptors as an amplification primer).

In certain embodiments, two adaptors sequences are ligated to the 5' ends of an insert, then the 3' ends of the insert are extended to copy the adaptor sequences. The copy of the adapter sequence becomes the priming site for the PCR primers, which are the same as the long, or ligation strand of the adapter. The long strand of the adapter represents some or preferably all of the sequence used in cluster formation in addition to barcodes, barcode priming sites and sequencer priming sites. The short oligo of the adapter can be ligatable to the 3' end (and get extended) or not ligate (only serves to enable DNA ligase to interact with the adapter, as the ligase is expecting dsDNA).

Optionally, a short oligo that does not ligate is used, therefore the 3' extension initiates at the 3' end of the DNA insert/fragment as opposed to 3' end of the short oligo. Using high concentrations of adapter ensure that sufficient un-ligated oligo will be available to serve as PCR primer. (If the short oligo is blocked at both ends, it cannot be ligated nor can it be extended, which makes for a cleaner library and less concern regarding interference in PCR. The scenario where adapter oligos are present but do not interfere with PCR is similar but now the residual ligated oligo of the adapter must either be diluted out with a longer oligo (to provide full sequence) or partially degraded to have a lower Tm than the oligos added for the PCR step).

Here we demonstrate that DNA library prep can be accomplished with only a single Bead cleanup after the PCR step. We demonstrate a workflow that is compatible with both mechanical and enzymatic shearing of DNA. We show the use of adaptors that allow for both ligation and PCR amplification, without addition of distinct PCR primers.

Benefits of the disclosure include methods in which post-ligation bead cleanup can be eliminated; a three step, single bead-cleanup protocol generates high quality libraries; and methods in which adaptors serve also as PCR primers.

Other embodiments are within the scope of the disclosure.

In some embodiments, methods of the disclosure include adding sequencing adaptors to DNA fragments (by ligation, hybridization, and extension) to form oligonucleotide extension products and amplifying the oligonucleotide extension products without any intervening purification or wash steps. When a sequencing library is prepared according to methods of the disclosure, material present after adaptor ligation—which may include excess molecular entities such as enzymes and adaptors as well as co-factors or other reagents—does not prevent a successful amplification reaction, which simplifies a library preparation workflow.

FIG. 1 diagrams a method 101 of library preparation. Methods include obtaining a obtaining 107 a plurality of DNA fragments from a sample. This may include obtaining a sample that includes nucleic acid to be sequenced and—where the nucleic acid is RNA, reverse transcribing the RNA into input DNA, and fragmenting the nucleic acid to yield DNA fragments. The DNA fragments are then end repaired 113 to provide blunt-end fragments. The DNA fragments are incubated with adaptors oligos, ligase, polymerase, and other reagents to ligate 125 a first adaptor oligos to the DNA fragments. A second adaptor oligo is hybridized to the fragments and extended to form oligonucleotide extension products. The oligonucleotide extension products are amplified 129 in the presence of excess material from the ligation to form a plurality amplicons, or library members. The library members may be used in the formation of sequencing clusters that may be sequenced 135.

Methods of the disclosure may be used to produce libraries used in next-generation sequencing starting with as little as 10 pg of double-stranded DNA. The library construction workflow is suitable for a wide range of sequencing applications including RNA-Seq, Digital Gene Expression (DGE), genomic DNA sequencing, target capture, amplicon sequencing, ChIP-Seq and more. These libraries are suitable for sequencing on Illumina sequencing platforms.

Figure 2:
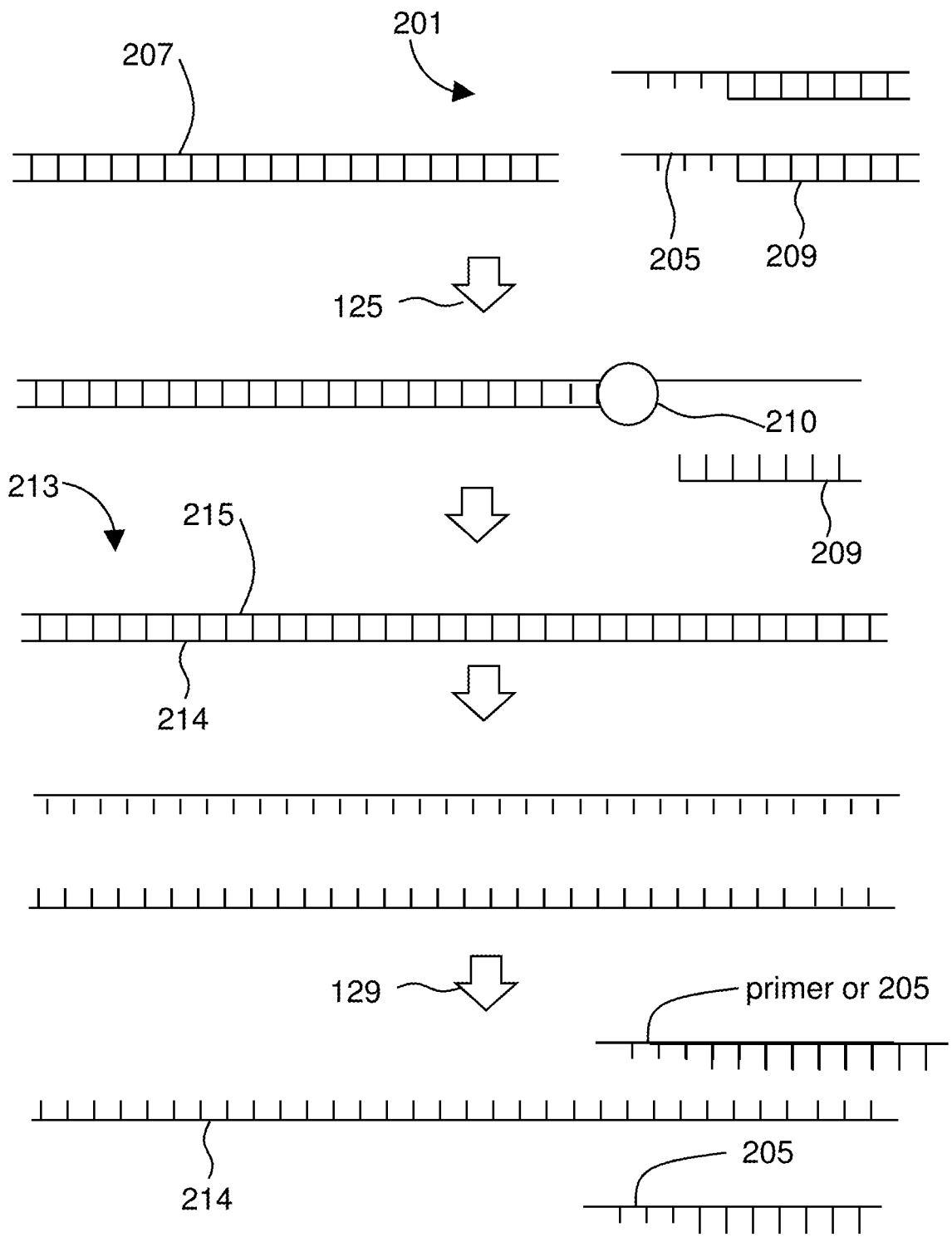
FIG. 2 illustrates operation of methods of the disclosure.

FIG. 2 illustrates operation of methods of the disclosure. Adaptors 201 are introduced to DNA fragments 207 (e.g., after end-repair 113). In the depicted embodiment, the adaptors 201 are added in excess and each includes a long strand 205 and a short strand 209. In the depicted embodiment, the 3' end of the long strand 205 is ligated to a free 5' end of a fragment 207 (the double-stranded portion of the adaptor 201 facilitates interaction with ligase). This adaptor addition 125 may include extending the fragment with a polymerase 210 (while, e.g., the short strand 209 is displaced).

The adaptor addition 125 yields adaptor-ligated fragments 213 which include an arbitrary sense strand 215 and a complementary strand 214. The adaptor-ligated fragments 213 proceed to amplification 129, which includes melting the adaptor-ligated fragments 213 and further includes hybridizing primers the arbitrary sense strand 215 and the complementary strand 214.

In an embodiment, the ligation adaptor oligos are not used as the library amplification primers. For example, the ligation adaptor oligos may not be full length. For example, the long adaptor oligo may be 30 bases from the 3' end of Illumina adaptors. In the amplification, the PCR primers can be added, which may be longer and add the rest of the full length Illumina adaptors to the amplified library.

Although there may be competition between PCR primers and the long adaptor oligos in the amplification, the full length library is still made (as shown by data in the appended Examples). Of several distinct embodiments (e.g., in which (i) adaptor oligo is present and competes with amplification primer; (ii) an adaptor oligo functions as an amplification primer; and/or (iii) a single-primer extension embodiment in which a first adaptor is ligated and a second adaptor hybridizes to and is extended over the first adaptor), in common among the embodiments is the lack of any requirement of a cleanup step or purification between adaptor addition and amplification.

Thus the disclosure provides a library preparation method in which adaptors are added to fragments which are then amplified without an intervening bead cleanup or purification step. Material from the adaptor addition step, including excess adaptor, may be present during the amplification and the included results show that those materials do not interfere with successful amplification to produce a library suitable for NGS sequencing.

In an optional embodiment, one of the primers is provided by the long strand 205 of the adaptors 201 (which adaptors 201 had been added in excess). The long strand 205 of the adaptor 201 thus hybridizes to the complementary strand 214 of the adaptor-ligated fragments 213 and is extended, at the core of the amplification 129 steps.

Illustrated were certain possible steps according to certain possible embodiments. In such embodiments, two adaptors sequences are ligated to the 5' ends of insert, then extend the 3' ends of insert to copy the adaptor sequences. The copy of the adapter sequence becomes the priming site for the PCR primers, which are the same as the long, or ligation strand of the adapter. In order for this to work, the long strand of the adapter now needs to represent the entire sequence used in cluster formation in addition to barcodes, barcode priming sites and sequencer priming sites. The short oligo in of the adapter can be ligatable to the 3' end (and get extended) or not ligate (only serves to enable DNA ligase to interact with the adapter—expecting ds DNA). It may be preferable to use a short oligo that does not ligate, such that the 3' extension initiates at the 3' end of the DNA insert/fragment as opposed to 3' end of the short oligo. Using high concentrations of adapter ensure that sufficient unligated oligo will be available to serve as PCR primer. The illustrated methods of DNA library prep can be accomplished with no more than a single bead cleanup after the PCR step. The workflow that is compatible with both mechanical and enzymatic shearing of DNA. The adaptors allow for both ligation and PCR amplification, without addition of distinct PCR primers.

Other embodiments are within the scope of the invention.

Figure 3:
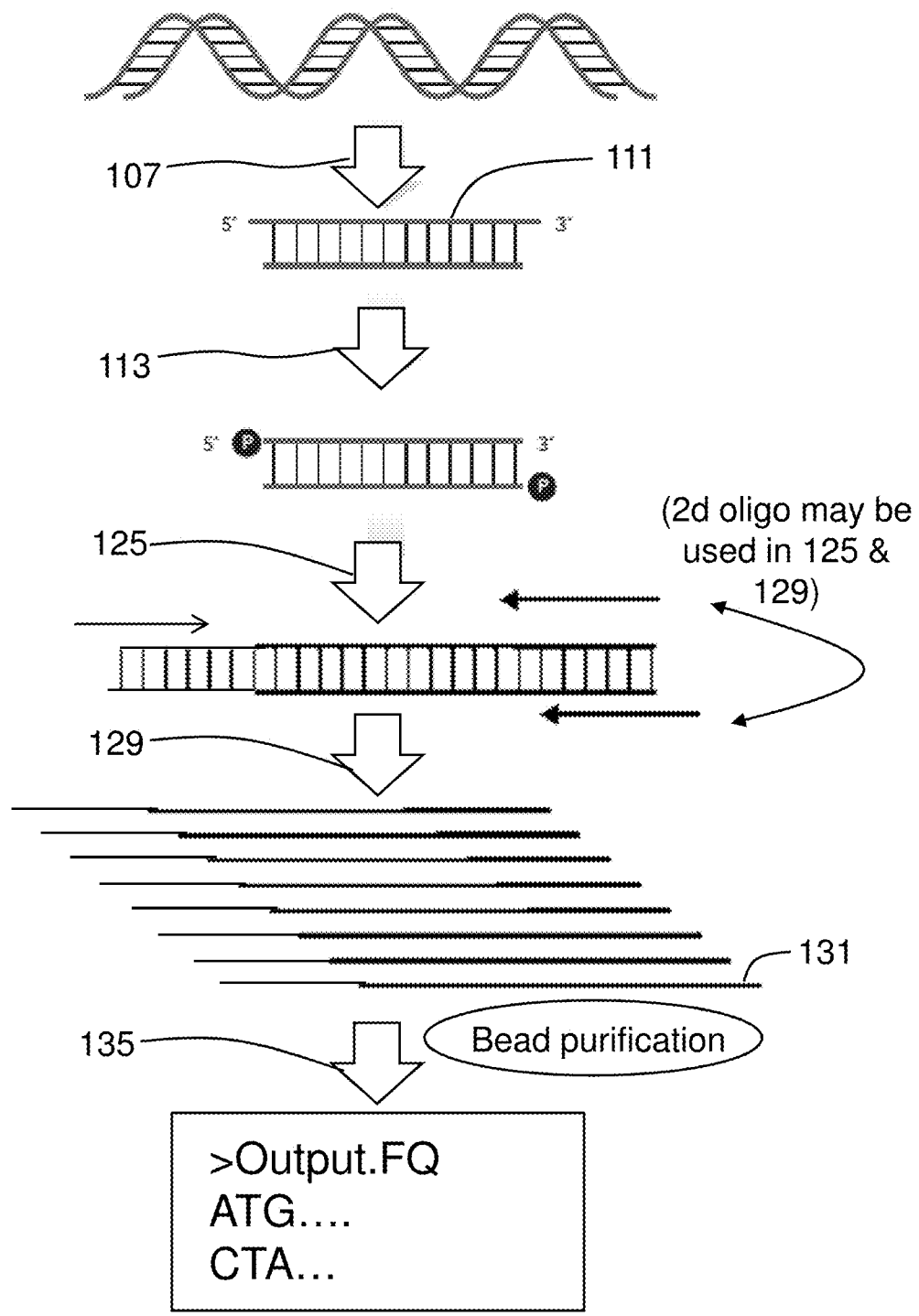
FIG. 3 shows steps of the method.

FIG. 3 shows steps of certain embodiments. The method may include fragmentation 107 of either genomic DNA or double-stranded cDNA, end repair 113 to generate blunt ends, adaptor addition 125 with optional multiplexing and PCR amplification 129 to produce the final library.

At step 125, the DNA fragments are incubated with adaptor oligos to form adaptor-ligated fragments in which at least a first adaptor oligo is ligated to a fragment and at least a second adaptor oligo hybridizes to the fragment and is extended by a polymerase to form a sequence complementary to a target and complementary to the first adaptor oligo. For details, see U.S. Pat. No. 9,650,628, incorporated by reference. Important sub-steps of forming the oligonucleotide extension products are stated as follows. The adaptor addition 125 includes (a) appending a first adaptor to a 5' end of each DNA fragment; (b) annealing second adapter oligos to the DNA fragments, whereby the second adapter oligos have a 3' portion that is complementary to a sequence of interest present in one or more of the fragments, and a 5' portion comprising a second adapter sequence; and (c) extending the second adapter oligos with a polymerase thereby generating one or more oligonucleotide extension products with the first adaptor at a first end and a second adaptor sequence at a second end.

The method 101 further includes amplifying 129 the oligonucleotide extension products in the presence of the adaptor oligos to form a plurality of amplicons. Copies of the second adaptor oligo function as primers during the amplification step. The entire workflow including fragmentation can be completed quickly, and yields DNA libraries ready for cluster formation and either single read or paired-end sequencing 135. Importantly, in the method 101 the steps of adaptor addition 125 and amplification 129 may be performed without an intervening purification step such as a bead wash. In fact, the second adaptor oligo of the ligation 125 step may serve as an amplification primer in the amplification step 129. Additionally, it may be found that other ligation materials (excess adaptors, co-factors such as Mg, PEG, enzymes such as ligase) simply do not interfere with amplification 129. Thus the method 101 may include (d) amplifying 129 the one or more oligonucleotide extension sion product using the second adaptor oligo as a primer. Methods may include steps described in U.S. Pat. No. 9,650,628, incorporated by reference for all purposes.

In addition to use with genomic and other double-stranded DNA sources, methods may be used with input RNA. Importantly, for DNA sequencing applications, low abundance samples can be input directly to the library construction workflow without the need for pre-amplification. Methods of the disclosure produce DNA libraries suitable for either single read or paired-end sequencing on sequencing platforms such as Illumina platforms, without the need for gel-based size selection.

Figure 4:
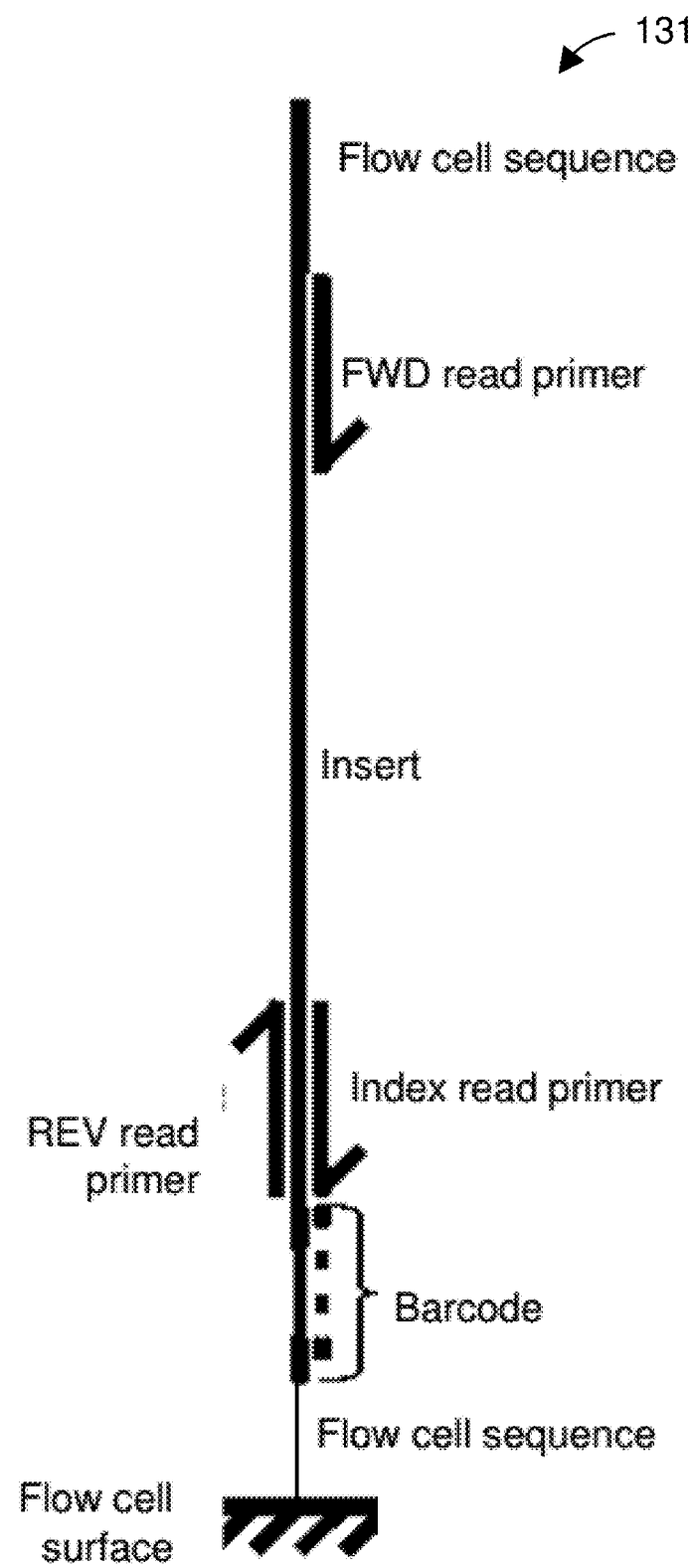
FIG. 4 shows a library member prepared according to the method.

FIG. 4 shows a library member prepared according to the method. Libraries suitable for cluster generation may be produced in a few hours using as little as 10 pg input of double-stranded DNA. Libraries produced according to the methods may include barcodes, e.g., 8 bp barcode sequences from reagent suppliers, which sequences may be input into sequencing software prior to data analysis.

The library preparation method 101 may include in three stages: DNA fragments are obtained 107 and the method further includes end repair of sheared DNA 313; adaptor ligation 325; and amplification 329. It may be preferable to use of a positive control DNA, to allow the establishment of a baseline of performance.

In general, the method will proceed according to a workflow that includes setting up and thawing the indicated reagents. Reagents and reaction tubes may be thawed, prepared, and kept on ice. After thawing and mixing buffer mixes, if any precipitate is observed, the buffers may be re-mixed/re-dissolved, gently warmed, and briefly vortexed. Generally, enzymes and primers are not warmed. Standard pipetting techniques are observed. Steps of the method 101 may be performed using a thermal cycler.

FIG. 5 diagrams an exemplary program for thermal cycler. Some embodiments employ a thermal cycler with a heat block designed for 0.2 mL tubes and equipped with a heated lid. Prepare the programs, following the operating instructions provided by the manufacturer. For thermal cyclers with an adjustable heated lid, set the lid temperature to 100 degrees C. only when sample temperature reaches above 30 degrees C. For thermal cyclers with a fixed temperature heated lid (e.g., ABI GENE AMP PCR 9600 and 9700 models), use the default settings (typically 100-105 degrees C.).

In some embodiments, the method 301 includes DNA fragmentation 307. Any suitable fragmentation method may be used including mechanical, chemical, or enzymatic fragmentation.

In certain embodiments, intact gDNA is diluted into 120 pL of 1× low-EDTA TE buffer, transferred into Covaris snap cap microtube, and fragmented to desired insert size following Covaris recommended settings.

Preferred embodiments of the method 101 include end repair 313. End repair 313 may include use of an end repair buffer mix (e.g., as sold by NuGEN Technologies, San Carlos, Calif.), end repair enzyme mix, end repair enhancer and nuclease-free water. The reagents are mixed and incubated according to manufacturer's instructions. The end-repair step 313 may proceed in a thermal-cycler programmed to run Program 1 (End Repair; see FIG. 5) or otherwise according to manufacturer's instructions.

After end repair 313, the blunt-ended fragments proceed to adaptor addition 125. Adaptors and associated reagents are added to the tubes according to manufacturer's instructions. In preferred embodiments, all samples intended to share the same sequencing flow cell lane should have unique ligation adaptors. In some embodiments, the ligation reaction will proceed in a thermal cycler (Ligation; see FIG. 5). Adaptor addition includes ligation of first adaptor, hybridization and extension of second adaptor, to form the oligonucleotide extension products.

An insight of the disclosure is that purification such as a bead wash after the adaptor addition 125 and before the amplification step 129 is not required and, in fact, an adaptor used in addition 125 can be carried over and used in amplification. After addition 125, excess adaptors (and other reagents or materials) may be present among the oligonucleotide extension products. Those excess materials may include magnesium or other metals, other co-factors, phosphate, polyethylene glycol (PEG), enzymes such as ligase, excess adapters, and blunt ended fragments.

Importantly, the method 101 may proceed without a purification step.

The method 101 proceeds to library amplification 129. For amplification, amplification enzymes, buffer, and primer mixes are added and mixed according to manufacturer's instructions. Amplification 129 may proceed in a pre-warmed thermal cycler programmed to run Program 3 (Library Amplification; see FIG. 5). Enrichment artifacts may be present after amplification 129. In some instances, PCR enrichment may create artifacts in the downstream library size analysis which appear as high molecular weight species during Bioanalyzer or gel analysis. This phenomenon is due to the amplification of diverse library molecules that have the same adaptor sequences at their termini. As the concentration of library molecules increases during PCR, the adaptor ends begin to compete with the PCR primers for hybridization, resulting in partially hybridized species. Although this may impact PCR efficiency, it does not impact library quality for subsequent sequencing, nor does it affect quantitation by qPCR.

After amplification 129, it may be desirable to perform purification 135 of the amplicons 131. For DNA purification, one may choose a nucleic acid column-based purification system that allows small volume elution, such as the reaction cleanup, it sold under the trademark MINELUTE by Qiagen. A bead-based purification protocol provided by Agencourt is described here for convenience.

Suspend beads in nuclease free water at room T by inverting and tapping tube.

Introduce bead suspension to DNA sample in microcentrifuge tubes & mix by pipetting.

Transfer the PCR tubes containing the bead-sample mixture to the magnet and let stand 5 minutes to completely clear the solution of beads.

Remove and discard binding buffer; wash with ethanol.

Air dry beads on magnet.

Add 1× low-EDTA TE buffer or nuclease-free water to the dried beads.

Transfer tubes to magnet; remove eluate

Remove from magnet and set aside.

For the bead purification step 135, follow the manufacturer's instructions. The above outline is given to aid in comprehension of the order of the steps. For precise reagents, timing, and volumes, see the manufacturer's instructions. Proceed to any QC steps such as any desired step for the quantitative and qualitative Assessment of the Library. One may optionally perform a Quantitative and Qualitative Assessment of the Library. Run the samples on the Bioanalyzer DNA 1000 Chip.

Sequences of the Barcodes in the Multiplexed Reactions Barcode sequences for the 32- and 96-plex Adaptor Plates are given in manufacturer's instructions. All barcode sequences are separated by an edit distance of three. For further details on the barcode design strategy, please refer to Faircloth BC, Glenn TC (2012) Not All Sequence Tags Are Created Equal: Designing and Validating Sequence Identification Tags Robust to Indels. PLoS ONE 7(8):e42543, incorporated by reference.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification, and guidance that can be adapted to the practice of this invention in its various embodiments and equivalents thereof.

EXAMPLES

Example 1. Traditional Library Prep Requires Post-Ligation Bead Cleanup

First, the effect of ligation reaction components on PCR was investigated by real-time PCR. Real-time PCR reactions using NuGEN OVATION Universal RNA-Seq System PCR reaction components, supplemented with a final 1× EvaGreen dye, were prepared with 10-fold serial dilutions of RNA-Seq library and 2-fold serial dilutions of ligation reaction components.

Figure 6:
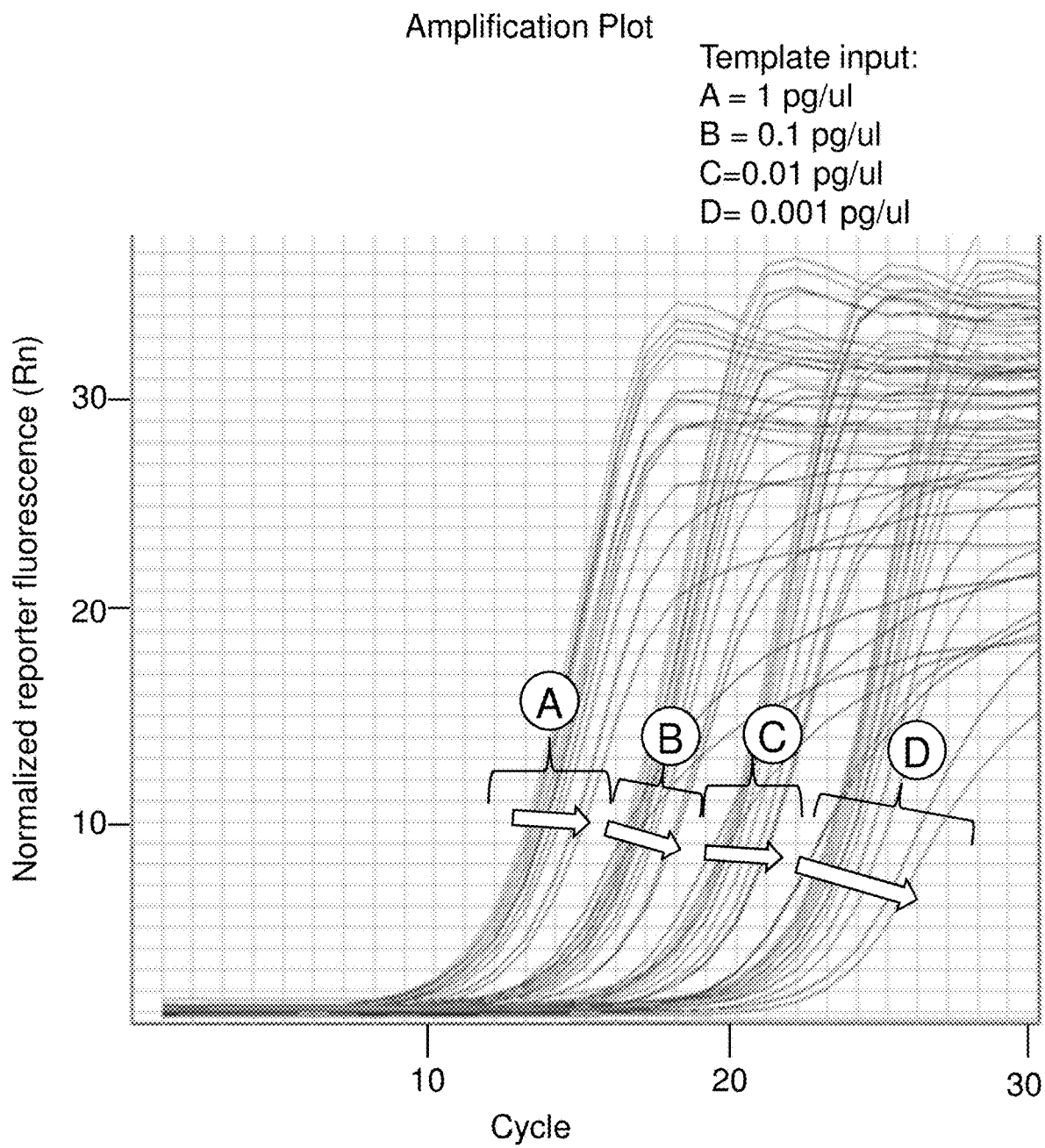
FIG. 6 shows the effect of ligation reaction components on PCR.

FIG. 6 shows the effect of ligation reaction components on PCR. Shown are the amplification curves of reactions containing 1.3 ul of 1 pg/ul, 0.1 pg/ul, 0.01 pg/ul and 0.001 pg/ul of RNA-seq library template, and an equal volume of ligation reaction components at 1×, 0.5×, 0.25×, 0.125×, 0.0.625×, 0.03125×, 0.015625×, or water. Compared to the standard PCR condition, the addition of ligation reaction components impairs PCR amplification by delaying the appearance of amplified products, and reducing the plateau of amplification. Next, we investigated the impact of eliminating the post-ligation bead purification by mixing ligation reactions directly into PCR at various ratios of ligation reaction to total PCR volume. Human genomic DNA was sheared by Covaris to 200 bp and 1 ng was used as input to end repair and ligation using reactions from the NuGEN OVATION Universal RNA-Seq System. After ligation, samples were either purified by Ampure beads or diluted directly into PCR reaction at a volume ratio of 1:2, 1:8, or 1:16. PCR products were purified by Ampure beads and analyzed by Bioanalyzer.

Figure 7:
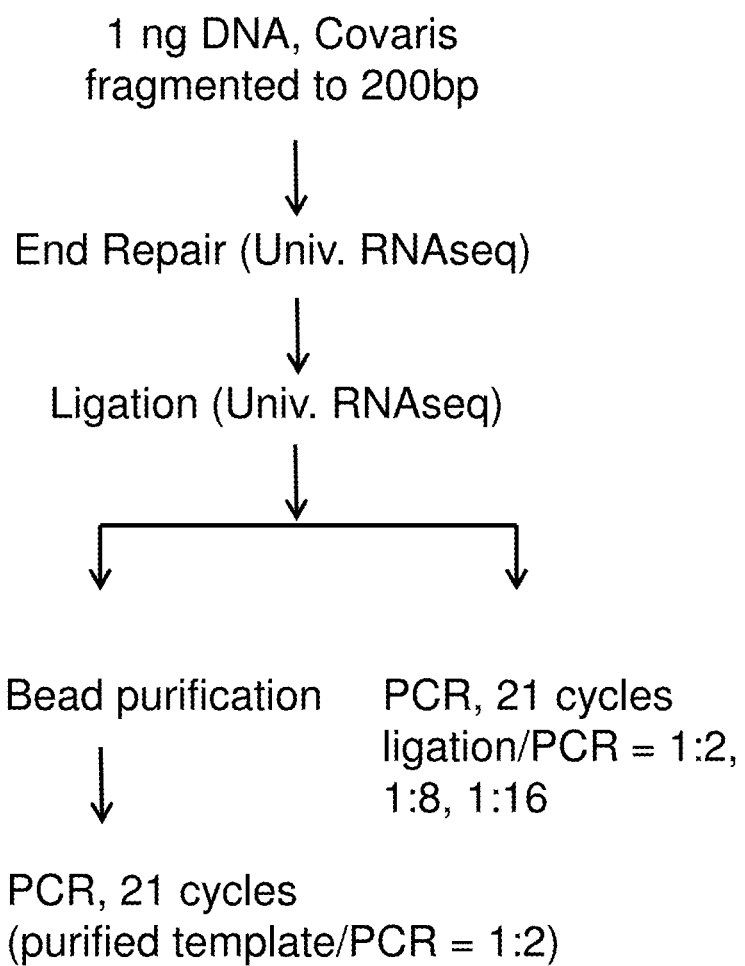
FIG. 7 shows the experimental set-up to show impact of eliminating the post-ligation bead purification.

FIG. 7 shows the experimental set-up to show impact of eliminating the post-ligation bead purification by mixing ligation reactions directly into PCR at various ratios of ligation reaction to total PCR volume.

Figure 8:
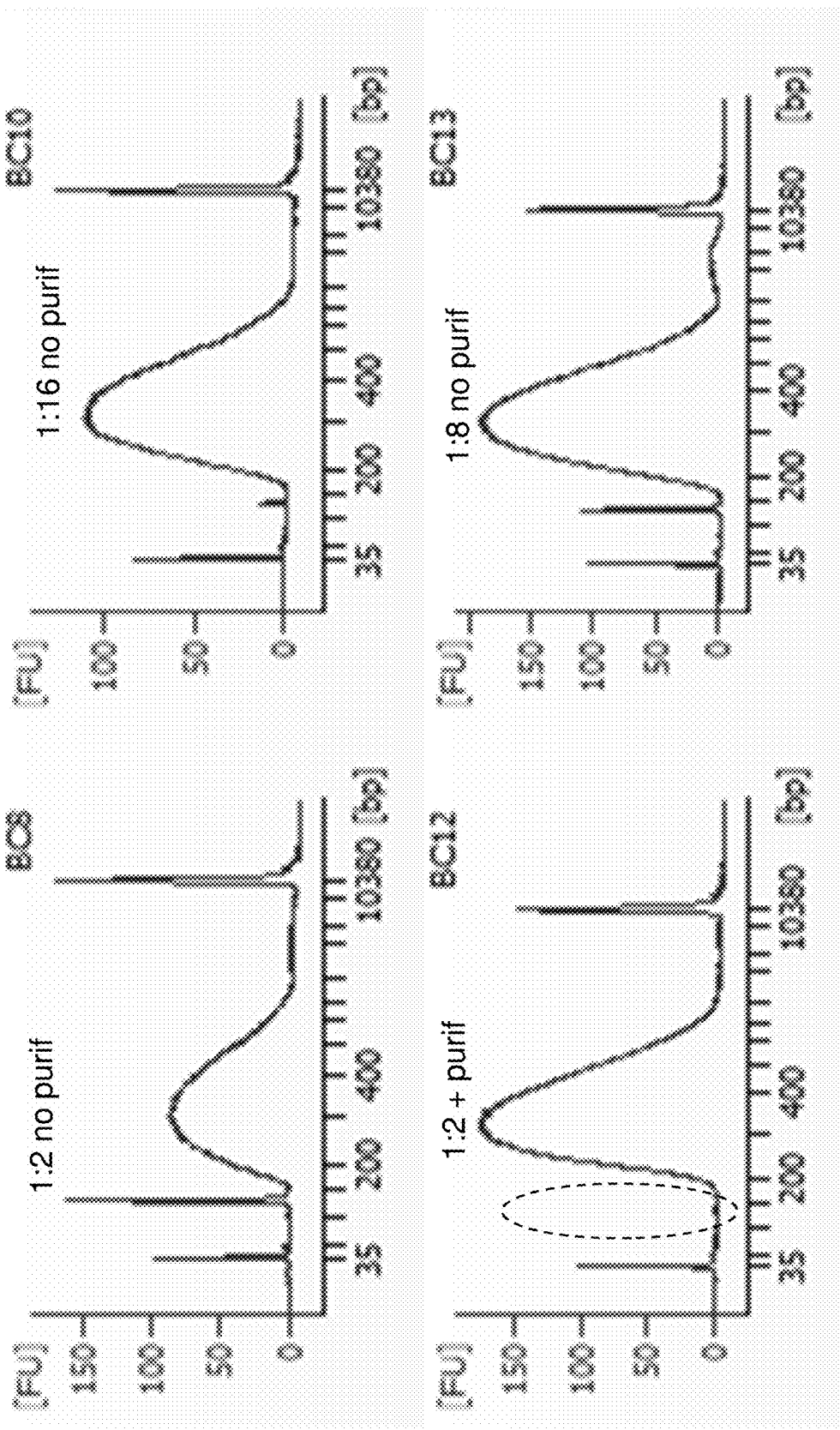
FIG. 8 gives results from the experiment to show impact of eliminating the post-ligation bead purification.

FIG. 8 bioanalyzer traces resulting from the experiment to show impact of eliminating the post-ligation bead purification. The traces clearly show that post-ligation bead purification is necessary to remove adaptor artifacts (the sharp peak at approximately 150 bp). Diluting the ligation reaction in a larger volume of PCR can reduce, but not eliminate these artifacts. Even at a ligation:total PCR volume ratio of 1:16, a small peak of adaptor artifact can be observed. The ligation volume for most NuGEN library prep kits, including Universal RNA-Seq and Ultralow v2, is 30 ul. A 1:16 ratio of ligation to PCR implies a PCR volume of 480 ul, which is costly and cumbersome to implement on modern thermocyclers which have a max volume per tube of 50 ul.

Example 2. Ligation Adaptors can Also Serve as PCR Primers

Adaptors supplied with the NuGEN OVATION Ultralow System V2 can serve as PCR primers. The surprising and unexpected result is that by eliminating the post-ligation bead purification and allowing the unligated adaptors to participate in PCR instead of adding the supplied PCR primers, robust amplification without adaptor artifacts could be achieved. This is demonstrated by using 100 ng or 10 ng of DNA fragmented to 300 bp by Covaris as input into the Ultralow v2 end repair and ligation reactions following the standard protocol. After ligation, which was performed in the standard 30 ul volume, 25.5 ul of Amp Buffer Mix, 2 ul of Amp Enzyme Mix, and 42.5 ul of water were added to prepare a 100 ul PCR reaction. The 100 ng and 10 ng reactions were subjected to 9 or 12 cycles of PCR following the cycling conditions described in the Ultralow user guide, respectively, then the PCR products were bead purified and analyzed by Bioanalyzer.

Methods of the disclosure may be used with a single-primer enrichment technology (SPET) target enrichment method as well as the UltraLow library system. In the ultralow method: two adaptors sequences are ligated to the 5' ends of insert; the 3' ends of insert are extended to copy the adaptor sequences. The copy of the adapter sequence becomes the priming site for the PCR primers, which are the same as the long, or ligation strand of the adapter.

In order for this to work, the long strand of the adapter now preferably represents the entire sequence used in cluster formation in addition to barcodes, barcode priming sites and sequencer priming sites. The short oligo in of the adapter can be ligatable to the 3' end (and get extended) or not ligate (only serves to enable DNA ligase to interact with the adapter—expecting ds DNA).

It may be preferable to use a short oligo that does not ligate, therefore the 3' extension initiates at the 3' end of the DNA insert/fragment as opposed to 3' end of the short oligo. Using high concentrations of adapter ensure that sufficient unligated oligo will be available to serve as PCR primer. If the short oligo is blocked at both ends, it can not be ligated nor can it be extended. This makes for a cleaner library and less concern regarding its interference in PCR. The scenario where adapter oligos are present but do not interfere with PCR is similar but now the residual ligated oligo of the adapter must either be diluted out with a longer oligo (to provide full sequence) or partially degraded to have a lower Tm than the oligos added for the PCR step.

Figure 9:
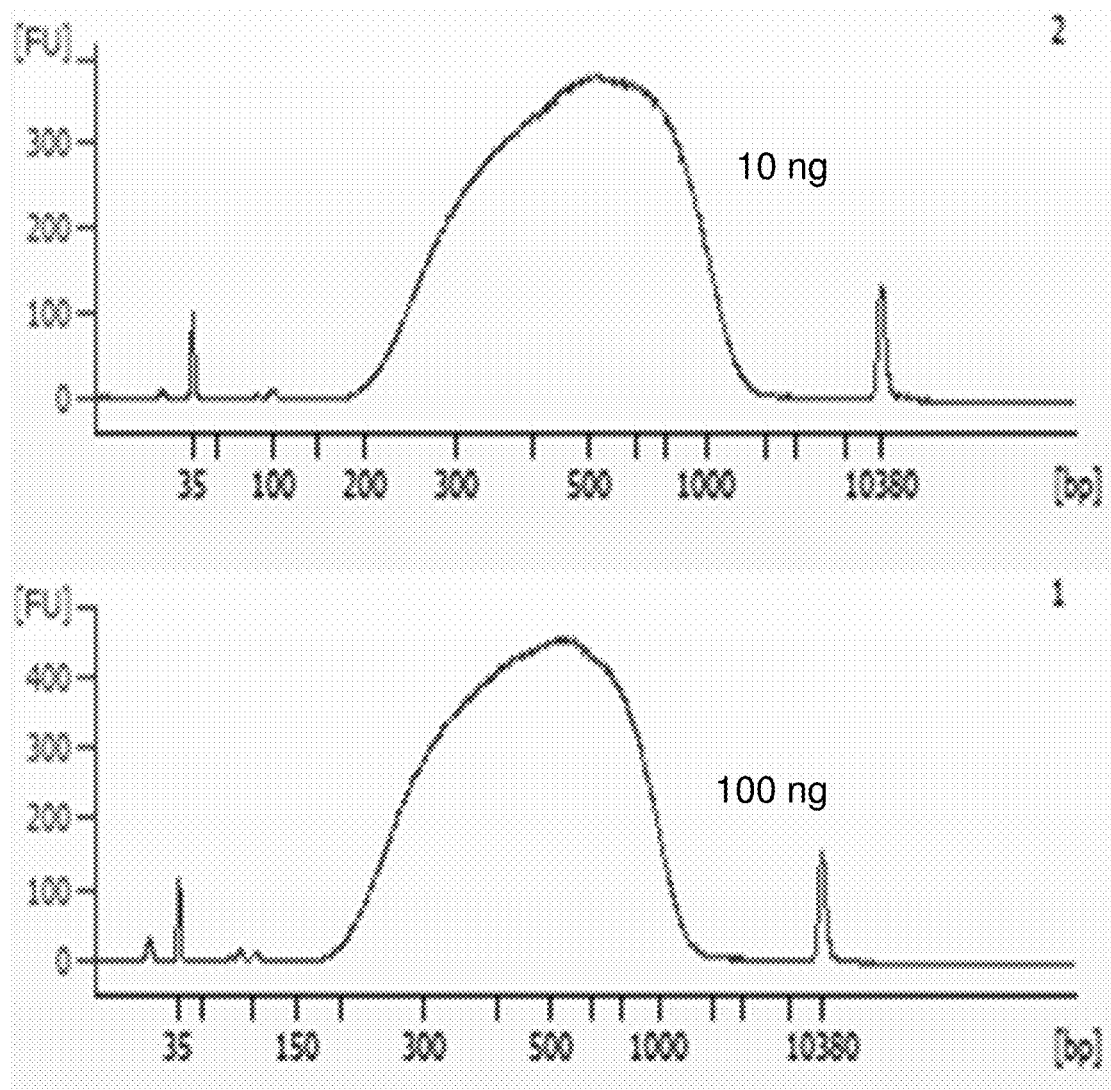
FIG. 9 shows results from inputting the DNA fragments into end repair and ligation reactions followed by PCR amplification.

FIG. 9 shows Bioanalyzer traces resulting from inputting the DNA fragments into end repair and ligation reactions followed by PCR amplification. The traces display normal looking libraries of the expected size and yield, with no evidence of adaptor artifacts, demonstrating the surprising ability of the NuGEN Ultralow adaptors to serve as PCR primers in the context of no post-ligation purification.

Based on the data, certain observations and conclusions may be made. The field of Next Generation Sequencing DNA library preparation is dominated by Illumina. One of their most widely used library prep kits is the TruSeq® Nano DNA Library Prep. Starting with fragmented DNA, the protocol consists of End Repair, Bead cleanup, A-tailing, Y-Adaptor Ligation, Bead cleanup, PCR, and a final Bead cleanup, for a total of 3 Bead cleanups and 5.5 hours to complete the protocol. A version of the NuGEN Ovation® Ultralow Library System offers a simplified workflow requiring only End Repair, Ligation, Bead cleanup, PCR, and a final Bead cleanup, for a total of two Bead cleanups and 4 hours to complete the protocol. It has been understood in the field that purification must be performed after ligation in order to remove adaptors and other ligation reaction components such as high concentrations of magnesium and PEG which are incompatible with the subsequent PCR step. Furthermore, both protocols require distinct PCR primers in order to amplify a functional final sequencing library.

Here, the data show that those long held beliefs are incorrect, and that DNA library prep can be accomplished with only a single Bead cleanup after the PCR step. The demonstrated workflow is compatible with both mechanical and enzymatic shearing of DNA. Here, NuGEN-style adaptors allow for both ligation and PCR amplification (i.e., with an adapter functioning as a PCR primer), without addition of distinct PCR primers (an approach not possible with the Illumina Y-adaptor approach).

Methods of the disclosure thus provide (1) a process whereby the post-ligation bead cleanup may be eliminated; (2) a three step, single bead cleanup protocol that generates high quality libraries; and (3) adaptors that serve also as PCR primers.

As shown in FIG. 8, the effect of ligation reaction components on PCR was investigated by real-time PCR, where it was clear that post-ligation bead purification was necessary to remove adaptor artifacts (the sharp peak at approximately 150 bp). Diluting the ligation reaction in a larger volume of PCR can reduce, but not eliminate these artifacts.

Here, we have shown that ligation adaptors can also serve as PCR primers. A surprising and unexpected result is that by eliminating the post-ligation bead purification and allowing the un-ligated adaptors to participate in PCR instead of adding the supplied PCR primers, robust amplification without adaptor artifacts could be achieved.

This is demonstrated by using 100 ng or 10 ng of DNA fragmented to 300 bp by Covaris as input into the Ultralow v2 end repair and ligation reactions following the standard protocol. After ligation, which was performed in the standard 30 ul volume, 25.5 ul of Amp Buffer Mix, 2 ul of Amp Enzyme Mix, and 42.5 ul of water were added to prepare a 100 ul PCR reaction. The 100 ng and 10 ng reactions were subjected to 9 or 12 cycles of PCR following the cycling conditions described in the Ultralow user guide, respectively, then the PCR products were bead purified and analyzed by Bioanalyzer. The resulting Bioanalyzer traces shown in FIG. 9 display normal looking libraries of the expected size and yield, with no evidence of adaptor artifacts, demonstrating the surprising ability of the NuGEN Ultralow adaptors to serve as PCR primers in the context of no post-ligation purification.

Example 3. Illumina Y-Adaptors Cannot Serve as PCR Primers

Figure 10:
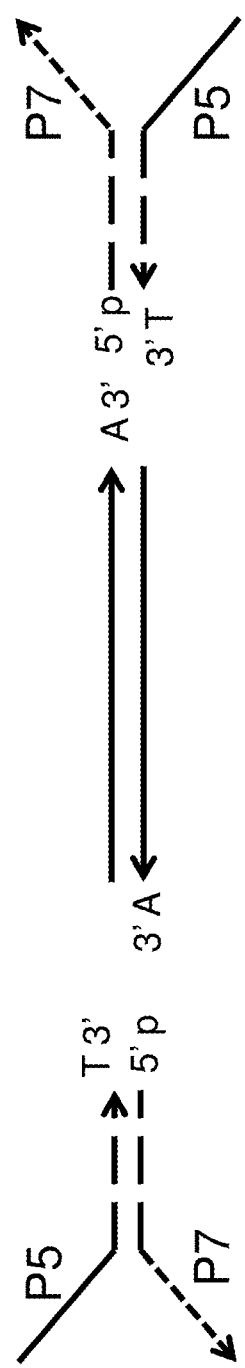
FIG. 10 diagrams Y-shaped adapters and a fragment.

FIG. 10 diagrams Y-shaped adapters, e.g., from Illumina (San Diego, Calif.), and a fragment. The Illumina Y-adaptors are ligated to A-tailed DNA inserts. Because of the structure of the adaptor oligos, the reverse complement of the adaptor cannot be generated. Therefore there is no possibility for un-ligated adaptor to serve as PCR primer, since there is no reverse complement primer binding site to allow the adaptor to anneal and extend during PCR.

Example 4. Present Invention is Compatible with Enzymatic Fragmentation

Intact genomic DNA was fragmented in a 15 ul reaction containing 2 mU HL-dsDNase (ArcticZymes), 6 U E. coli DNA Polymerase I (NEB), 1.5 U T4 DNA Polymerase, 1×NEBuffer 2 (NEB) and 0.2 mM dNTPs under the following temperature profile: 25 C for 15 min, 65 C for 15 min, 4 C hold. The NuGEN Ultralow v2 ligation and PCR components were used to perform ligation and PCR as follows. Ligation was performed by adding 3 ul of Ligation Adaptor Mix, 5 ul of Ligation Buffer Mix, and 2 ul of Ligation Enzyme Mix for a total of 25 ul. After the standard ligation incubation steps of 25 C for 30 min, 70 C for 10 min, and 4 C hold, PCR components were added directly to the ligation reaction, without bead purification. 25.5 ul of Amp Buffer Mix, 2.5 ul of Amp Primer Mix, 2 ul of Amp Enzyme Mix, and 45 ul of water were added to prepare a 100 ul PCR reaction. After 9 cycles of PCR following the cycling conditions described in the Ultralow user guide the PCR products were bead purified and analyzed by Bioanalyzer.

Figure 11:
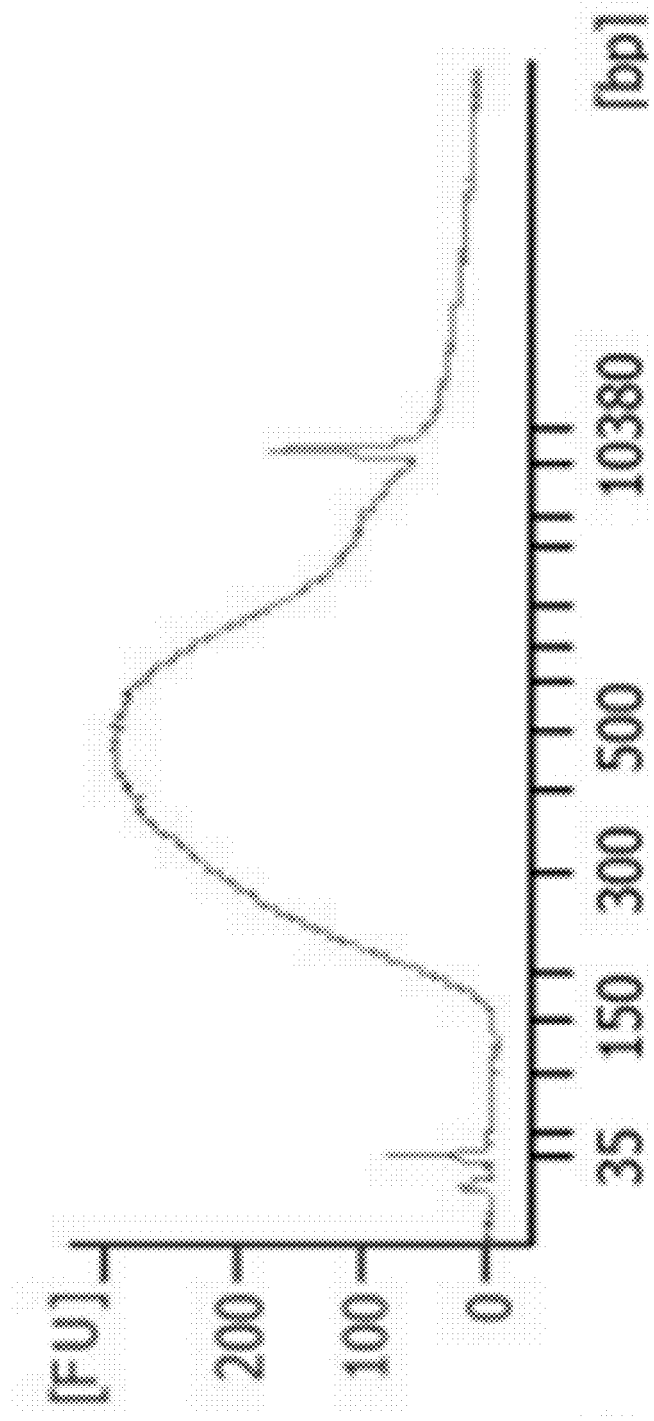
FIG. 11 shows traces of library prepared by adapter-ligation and amplification of enzymatically fragmented nucleic acid.

FIG. 11 shows Bioanalyzer traces of library prepared by adapter-ligation and amplification of enzymatically fragmented nucleic acid. The resulting Bioanalyzer traces display normal looking libraries of the expected size and yield, with no evidence of adaptor artifacts, demonstrating the compatibility of no post-ligation purification with enzymatic fragmentation.

REFERENCES

TRUSEQ Nano DNA Library Prep guide, file name truseq-nano-dna-library-prep-guide-15041110-d.pdf, available from support.illumina.com, Illumina, Inc., San Diego, Calif. (40 pages)

The OVATION Ultralow System V2 User guide, part No. 0344, 0344NB, file name M01379_v5_User_Guide_Ovation_Ultralow_Library_Systems_V2_(Part_No._0344)_2215.pdf, available from nugen.com from NuGEN Technologies Inc., San Carlos, Calif. (30 pages).

What is claimed is:

1. A method of preparing a sequencing library, the method comprising:
   obtaining a plurality of DNA fragments from a sample;
   introducing at least partially double-stranded adaptors to the plurality of DNA fragments;
   ligating a first strand of the adaptors to 5' ends of the DNA fragments to form adaptor-ligated fragments; and
   amplifying without purifying the adaptor-ligated fragments in the presence of excess adaptors not ligated to one of the DNA fragments to form a plurality of amplicons, wherein the first strand comprises a barcode sequence.

2. The method of claim 1, wherein amplifying the adaptor-ligated fragments includes adding amplification primers that compete with the first strand of the adaptors.

3. The method of claim 1, further comprising extending a free 3' end of the DNA fragment by polymerase to copy the first strand of the adaptor.

4. The method of claim 1, wherein the first strand of the adaptor is at least a few nucleotides longer than a second strand of the adaptor.

5. The method of claim 1, wherein amplifying the adaptor-ligated fragments includes using the first strand of the adaptor as an amplification primer.

6. The method of claim 1, further comprising purifying the amplicons to remove excess material.

7. The method of claim 1, further comprising attaching the amplicons to the surface of a flow cell surface to form sequencing clusters.

8. The method of claim 1, further comprising fragmenting a nucleic acid from the sample to obtain the plurality of DNA fragments.

9. The method of claim 1, wherein the amplification step occurs in the presence of excess ligation reagents that include one or more of co-factors, enzymes, and polyethylene glycol.

10. A method of preparing a sequencing library, the method comprising:
    obtaining a plurality of DNA fragments from nucleic acid from a sample;
    incubating the DNA fragments with adaptor oligos to form oligonucleotide extension products, wherein at least a first adaptor oligo is ligated to a fragment and at least a second adaptor oligo hybridizes to the fragment and is extended by a polymerase to form a sequence complementary to a target and complementary to the first adaptor oligo; and
    amplifying without purifying the oligonucleotide extension products in the presence of excess adaptor oligos not ligated to one of the DNA fragments to form a plurality of amplicons, wherein the first adapter oligo comprises a barcode sequence.

11. The method of claim 10, wherein copies of the second adaptor oligo function as primers during the amplification step.

12. The method of claim 10, further comprising purifying the amplicons to remove excess material.

13. The method of claim 10, further comprising attaching the amplicons to a flow cell surface to form sequencing clusters.

14. The method of claim 13, further comprising sequencing the amplicons to determine a sequence of the nucleic acid.

15. The method of claim 10, further comprising fragmenting the nucleic acid from the sample to obtain the plurality of DNA fragments.

16. The method of claim 10, wherein the amplification step occurs in the presence of excess ligation reagents that include one or more of co-factors, enzymes, and polyethylene glycol.

17. The method of claim 1, wherein the first strand comprises one or more of a sequence used in cluster formation, one or more barcode priming site, and one or more sequencer priming site.

18. The method of claim 10, wherein the first adapter oligo comprises one or more of a sequence used in cluster formation, one or more barcode priming site, and one or more sequencer priming site.

\* \* \* \* \*